(12) United States Patent
Brenizer et al.

(10) Patent No.: US 10,722,252 B2
(45) Date of Patent: Jul. 28, 2020

(54) SUBINTIMAL CATHETER DEVICE, ASSEMBLY AND RELATED METHODS

(71) Applicant: Teleflex Life Sciences Limited, Valletta (MT)

(72) Inventors: Joshua Brenizer, Maple Grove, MN (US); Jesse Leonard Farris, III, Andover, MA (US); Thomas Kouchoukos, Edina, MN (US); Mark Wendle, Minneapolis, MN (US); Brandon VanHee, Ostego, MN (US); Dean Peterson, Minneapolis, MN (US); Steve Michael, New Hope, MN (US); Alexander Marine, Excelsior, MN (US); Lyndon Carlson, Southlake, TX (US)

(73) Assignee: Teleflex Life Sciences Limited, Valletta (MT)

( * ) Notice: Subject to any disclaimer, the term of this patent is extended or adjusted under 35 U.S.C. 154(b) by 186 days.

(21) Appl. No.: 16/160,162

(22) Filed: Oct. 15, 2018

(65) Prior Publication Data

US 2019/0125373 A1 May 2, 2019

Related U.S. Application Data

(60) Provisional application No. 62/577,283, filed on Oct. 26, 2017.

(51) Int. Cl.
*A61B 17/22* (2006.01)
*A61M 25/00* (2006.01)
(Continued)

(52) U.S. Cl.
CPC ........ *A61B 17/22* (2013.01); *A61B 17/00234* (2013.01); *A61B 90/39* (2016.02);
(Continued)

(58) Field of Classification Search
CPC ........ A61B 17/3207; A61B 17/320733; A61B 2017/302741; A61B 2017/320008;
(Continued)

(56) References Cited

U.S. PATENT DOCUMENTS

| 3,452,742 A | 7/1969 | Muller |
| 4,846,186 A | 7/1989 | Box et al. |

(Continued)

FOREIGN PATENT DOCUMENTS

| EP | 0468645 A1 | 1/1992 |
| EP | 0495299 A1 | 7/1992 |

(Continued)

OTHER PUBLICATIONS

PCT International Search Report dated Feb. 5, 2019 in application No. PCT/US2018/055832.

(Continued)

*Primary Examiner* — Wade Miles
(74) *Attorney, Agent, or Firm* — Gregory W. Smock

(57) ABSTRACT

Catheter devices, assemblies and related methods for percutaneous crossing of an occlusion in a blood vessel are disclosed. A catheter device can include a central catheter, two side tubes, and a distally-protruding, curved subintimal guidewire. The central catheter can define a central lumen that extends from a proximal end to a distal end of the central catheter. The lumen can be configured to receive a primary guidewire. The central catheter can also define at least one reentry aperture oriented transverse to the central lumen. The first and second side tubes can be coupled with the central catheter, extending along a longitudinal axis thereof, with the first side tube flanking an opposite side of the central catheter relative to the second side tube. The subin- (Continued)

timal guidewire can extend from the first side tube, distally beyond the distal end of the central catheter, to the second side tube.

22 Claims, 8 Drawing Sheets

(51) Int. Cl.
*A61M 25/09* (2006.01)
*A61M 25/01* (2006.01)
*A61B 90/00* (2016.01)
*A61B 17/00* (2006.01)

(52) U.S. Cl.
CPC ............ *A61M 25/0194* (2013.01); *A61B 2017/00292* (2013.01); *A61B 2017/22045* (2013.01); *A61B 2017/22051* (2013.01); *A61B 2017/22095* (2013.01); *A61B 2090/3966* (2016.02); *A61M 25/0021* (2013.01); *A61M 25/0108* (2013.01); *A61M 25/0147* (2013.01); *A61M 2025/018* (2013.01); *A61M 2025/0177* (2013.01); *A61M 2025/0197* (2013.01); *A61M 2025/09008* (2013.01)

(58) Field of Classification Search
CPC .......... A61B 17/22; A61B 17/221; A61B 2017/2212; A61M 2025/0037
See application file for complete search history.

(56) References Cited

U.S. PATENT DOCUMENTS

| | | | |
|---|---|---|---|
| 5,303,714 A | 4/1994 | Abele et al. | |
| 5,385,152 A | 1/1995 | Abele et al. | |
| 5,505,699 A | 4/1996 | Forman et al. | |
| 5,728,122 A | 3/1998 | Leschinsky et al. | |
| 5,938,623 A | 8/1999 | Quiachon et al. | |
| RE37,148 E | 4/2001 | Shank | |
| 6,211,049 B1 | 4/2001 | Farrar | |
| 6,217,527 B1 | 4/2001 | Selmon et al. | |
| 6,231,546 B1 | 5/2001 | Milo et al. | |
| 6,235,000 B1 | 5/2001 | Milo et al. | |
| 6,254,550 B1 | 7/2001 | McNamara et al. | |
| 6,464,650 B2 | 10/2002 | Jafari et al. | |
| 6,500,130 B2 | 12/2002 | Kinsella et al. | |
| 6,511,458 B2 | 1/2003 | Milo et al. | |
| 6,514,217 B1 | 2/2003 | Selmon et al. | |
| 6,638,266 B2 | 10/2003 | Wilson et al. | |
| 6,719,725 B2 | 4/2004 | Milo et al. | |
| 6,761,696 B1 | 7/2004 | Wong | |
| 7,004,173 B2 | 2/2006 | Sparks et al. | |
| 7,128,718 B2 | 10/2006 | Hojeibane et al. | |
| 7,294,139 B1* | 11/2007 | Gengler | A61B 17/221 606/113 |
| 7,520,863 B2 | 4/2009 | Grewe et al. | |
| 7,715,903 B2 | 5/2010 | Hartley et al. | |
| 7,785,273 B2 | 8/2010 | Eskuri | |
| 7,785,274 B2 | 8/2010 | Mishima et al. | |
| 7,938,819 B2 | 5/2011 | Kugler et al. | |
| 7,942,832 B2 | 5/2011 | Kanuka et al. | |
| 8,022,331 B2 | 9/2011 | Reynolds et al. | |
| 8,083,727 B2 | 12/2011 | Kugler et al. | |
| 8,202,246 B2 | 6/2012 | Kugler et al. | |
| 8,226,566 B2 | 7/2012 | Nita | |
| 8,241,311 B2 | 8/2012 | Ward et al. | |
| 8,252,015 B2 | 8/2012 | Leeflang et al. | |
| 8,257,278 B2 | 9/2012 | Howland et al. | |
| 8,257,382 B2 | 9/2012 | Rottenberg et al. | |
| 8,257,383 B2 | 9/2012 | Rottenberg et al. | |
| 8,277,469 B2 | 10/2012 | Carmeli et al. | |
| 8,313,445 B2 | 11/2012 | Mishima et al. | |
| 8,323,261 B2 | 12/2012 | Kugler et al. | |
| 8,337,425 B2 | 12/2012 | Olson et al. | |
| 8,374,680 B2 | 2/2013 | Thompson | |
| 8,376,961 B2 | 2/2013 | Layman et al. | |
| 8,512,310 B2 | 8/2013 | Kugler et al. | |
| 8,551,020 B2 | 10/2013 | Chen et al. | |
| 8,679,049 B2 | 3/2014 | Nita | |
| 8,721,675 B2 | 5/2014 | Rottenberg et al. | |
| 8,920,449 B2 | 12/2014 | Wilkinson | |
| 8,932,315 B2 | 1/2015 | Brian et al. | |
| 8,956,376 B2 | 2/2015 | Alvarez et al. | |
| 8,961,494 B2 | 2/2015 | Kugler et al. | |
| 8,998,936 B2 | 4/2015 | Alvarez et al. | |
| 9,060,802 B2 | 6/2015 | Kugler et al. | |
| 9,174,032 B2 | 11/2015 | Zhou et al. | |
| 9,272,121 B2 | 3/2016 | Piccagli | |
| 9,278,192 B2 | 3/2016 | Copeta et al. | |
| 9,301,774 B2 | 4/2016 | O'Day | |
| 9,308,019 B2 | 4/2016 | Kugler et al. | |
| 9,320,874 B2 | 4/2016 | Sina | |
| 9,402,646 B2 | 8/2016 | Nita | |
| 9,402,649 B2 | 8/2016 | Brian et al. | |
| 9,402,981 B2 | 8/2016 | Anderson | |
| 9,408,998 B2 | 8/2016 | Alvarez et al. | |
| 9,451,984 B2 | 9/2016 | Zhou et al. | |
| 9,486,239 B2 | 11/2016 | Anderson et al. | |
| 9,579,489 B2 | 2/2017 | Zhou et al. | |
| 9,603,615 B2 | 3/2017 | Sarge | |
| 9,717,889 B2 | 8/2017 | Kugler et al. | |
| 10,391,282 B2 | 8/2019 | Root et al. | |
| 2002/0082523 A1 | 6/2002 | Kinsella et al. | |
| 2002/0183654 A1 | 12/2002 | Zhou | |
| 2004/0073141 A1 | 4/2004 | Hartley et al. | |
| 2004/0193151 A1 | 9/2004 | To et al. | |
| 2004/0199088 A1 | 10/2004 | Bakos et al. | |
| 2007/0219464 A1 | 9/2007 | Davis et al. | |
| 2008/0004606 A1 | 1/2008 | Swain et al. | |
| 2008/0064988 A1 | 3/2008 | Carter et al. | |
| 2008/0228171 A1 | 9/2008 | Kugler et al. | |
| 2008/0269641 A1 | 10/2008 | Coyle | |
| 2010/0228151 A1 | 9/2010 | Carmeli et al. | |
| 2011/0098648 A1 | 4/2011 | Kato | |
| 2011/0276079 A1 | 11/2011 | Kugler et al. | |
| 2012/0095485 A1 | 4/2012 | Cully et al. | |
| 2012/0123329 A1 | 5/2012 | Kato | |
| 2012/0158021 A1 | 6/2012 | Morrill | |
| 2012/0239073 A1 | 9/2012 | Hubregtse et al. | |
| 2012/0323251 A1 | 12/2012 | Kugler et al. | |
| 2013/0046286 A1 | 2/2013 | Simpson | |
| 2013/0110144 A1 | 5/2013 | Olson et al. | |
| 2013/0238003 A1 | 9/2013 | Fischer et al. | |
| 2013/0245430 A1 | 9/2013 | Selmon et al. | |
| 2013/0317534 A1 | 11/2013 | Zhou et al. | |
| 2014/0046216 A1 | 2/2014 | Palme et al. | |
| 2014/0121689 A1 | 5/2014 | Kugler et al. | |
| 2014/0275983 A1 | 9/2014 | Piccagli | |
| 2014/0276911 A1* | 9/2014 | Smith | A61B 17/32056 606/113 |
| 2014/0277053 A1 | 9/2014 | Wang et al. | |
| 2014/0277068 A1 | 9/2014 | Kugler et al. | |
| 2014/0371718 A1 | 12/2014 | Alvarez et al. | |
| 2015/0051633 A1 | 2/2015 | Sina | |
| 2015/0080928 A1 | 3/2015 | Kugler et al. | |
| 2015/0148706 A1 | 5/2015 | Abner | |
| 2015/0165163 A1 | 6/2015 | Alvarez et al. | |
| 2015/0320975 A1 | 11/2015 | Simpson et al. | |
| 2016/0008015 A1* | 1/2016 | Nguyen | A61B 17/221 606/127 |
| 2016/0008584 A1 | 1/2016 | Root et al. | |
| 2016/0045713 A1 | 2/2016 | Waisman et al. | |
| 2016/0074627 A1 | 3/2016 | Cottone | |
| 2016/0081709 A1 | 3/2016 | Majercak | |
| 2016/0157872 A1 | 6/2016 | Cage et al. | |
| 2016/0183953 A1 | 6/2016 | Kugler et al. | |
| 2016/0192952 A1 | 7/2016 | Warren | |
| 2016/0206334 A1 | 7/2016 | Rizk et al. | |
| 2016/0213386 A1 | 7/2016 | Wilkinson | |
| 2016/0235948 A1 | 8/2016 | Sina | |
| 2016/0242795 A1* | 8/2016 | Iwabuchi | A61B 17/221 |
| 2016/0250448 A1 | 9/2016 | Copeta et al. | |
| 2016/0271374 A1 | 9/2016 | Spencer | |

(56) References Cited

U.S. PATENT DOCUMENTS

| | | | |
|---|---|---|---|
| 2016/0287273 A1* | 10/2016 | Honda | A61B 17/22 |
| 2016/0302807 A1 | 10/2016 | Anderson | |
| 2016/0317175 A1 | 11/2016 | Remmerswaal et al. | |
| 2016/0331567 A1 | 11/2016 | Nita | |
| 2016/0338721 A1 | 11/2016 | Alvarez et al. | |
| 2016/0346002 A1* | 12/2016 | Avneri | A61B 17/32056 |
| 2016/0361076 A1 | 12/2016 | Zhou et al. | |
| 2017/0020563 A1 | 1/2017 | Anderson et al. | |
| 2017/0049472 A1* | 2/2017 | Uihlein | A61B 17/221 |
| 2017/0079671 A1 | 3/2017 | Morero et al. | |
| 2017/0100141 A1 | 4/2017 | Morero et al. | |
| 2017/0128090 A1 | 5/2017 | Sarge | |
| 2017/0172653 A1 | 6/2017 | Urbanski et al. | |
| 2018/0000513 A1 | 1/2018 | Kugler et al. | |
| 2018/0049759 A1* | 2/2018 | Thomas | A61B 17/22 |
| 2018/0256179 A1* | 9/2018 | Hayakawa | A61B 17/22031 |
| 2018/0325538 A1* | 11/2018 | Ambroze | A61B 17/22031 |

FOREIGN PATENT DOCUMENTS

| | | |
|---|---|---|
| EP | 0778042 B1 | 3/2000 |
| EP | 1419794 B1 | 11/2009 |
| EP | 2700368 B1 | 2/2015 |
| EP | 2636381 B1 | 3/2018 |
| WO | 1998005376 A1 | 2/1998 |
| WO | 2002096492 A2 | 12/2002 |
| WO | 2004018031 A2 | 3/2004 |
| WO | 2006039217 A1 | 4/2006 |
| WO | 2007121002 A1 | 10/2007 |
| WO | 2010087953 A1 | 8/2010 |
| WO | 2010092347 A1 | 8/2010 |
| WO | 2010115163 A9 | 7/2011 |

OTHER PUBLICATIONS

PCT Written Opinion dated Feb. 5, 2019 in application No. PCT/US2018/055832.

Scholtes, Vincent P.W. et al. "Subintimal Angioplasty Track of the Superficial Femoral Artery: A Histological Analysis," Circulation: Cardiovascular Interventions, published by American Heart Association, Dallas, TX, p. e6-e8 (Feb. 2012).

* cited by examiner

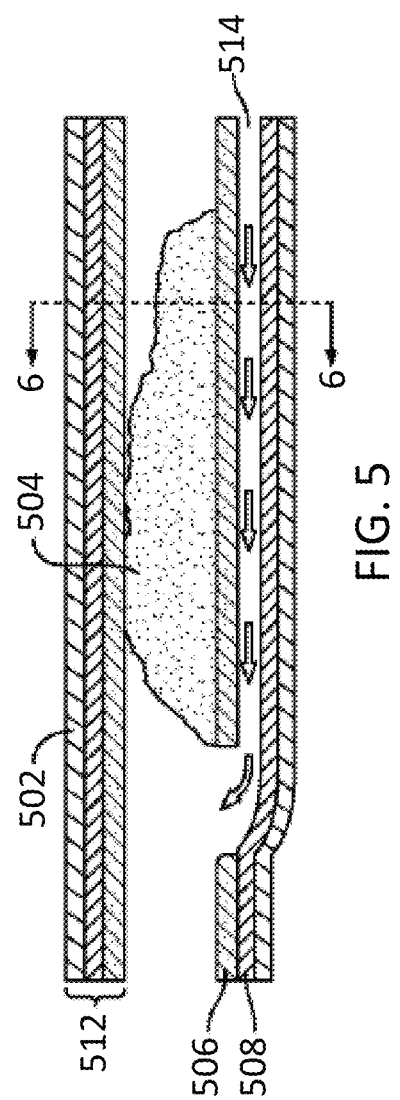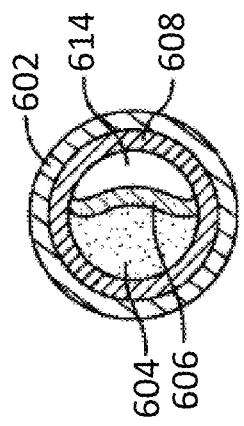

SUBINTIMAL CATHETER DEVICE, ASSEMBLY AND RELATED METHODS

CLAIM OF PRIORITY

This non-provisional patent document claims the benefit of priority under 35 U.S.C. § 119(e) to U.S. Provisional Patent Application Ser. No. 62/577,283, entitled "SUBINTIMAL CATHETER DEVICE, ASSEMBLY AND RELATED METHODS" and filed on Oct. 26, 2017, which is herein incorporated by reference in its entirety.

TECHNICAL FIELD

This application relates to the field of minimally invasive catheterization. Particular implementations relate to devices, assemblies and methods for percutaneous circumvention of an occlusion in a blood vessel.

BACKGROUND

The build-up of plaque in blood vessels is common and causes may life-threatening events, such as heart attacks and strokes. Atherosclerotic plaque, for example, is known to accumulate in arterial walls of the human body. This plaque build-up restricts circulation and can result in cardiovascular problems, particularly when the build-up occurs in coronary arteries.

A method for opening a partially occluded blood vessel is to guide one or more medical devices to a diseased, e.g., occluded, site where they can be used to carry out treatment. A guidewire is often used for guiding a catheter or other treatment device toward the diseased site. The distal tip of the guidewire can be introduced into the body of a treated subject by means of a needle or other access device, which pierces the subject's skin, and advanced to the site. The catheter or other treatment device can then be threaded over the guidewire and advanced through internal blood vessel passages to the diseased site using the guidewire as a rail.

Total or near-total occlusions can block passage through portions of a blood vessel. In subjects suffering from a coronary chronic total occlusion (CTO), for example, successful treatment of the occlusion can be challenging. A factor that can determine whether a user, e.g., a treating clinician, can successfully treat the occlusion is the clinician's ability to advance a guidewire from a location proximal of the occlusion to a location distal of the occlusion. In some instances, such as when the occlusive matter is soft or where the occlusion has a tiny opening, the guidewire can be forced through the occlusive matter and allowed to remain within the natural or true lumen of the blood vessel. In other instances, such as when the true lumen of the blood vessel is totally occluded by hard plaque (e.g., calcified atherosclerotic plaque), the guidewire cannot cross the occlusion and, in response to a continued proximally-applied pushing force, may permanently kink and/or its distal end portion may deviate to an adjacent vessel wall and perforate the vessel.

Overview

The present inventors recognize that existing methods for treating an occluded site within a blood vessel often require exchanging a plurality of separate medical devices, each of which needs to be successfully advanced to the occlusion in stepwise fashion. Preexisting devices may be likely to puncture non-targeted layers of a blood vessel wall and may provide only a small reentry pathway back into the true lumen, distal to an occlusion, which is susceptible to becoming lost during an operation and becoming re-sealed or obstructed. New devices, assemblies and methods of using them are thus needed to reduce the number of separate medical devices necessary to treat an occlusion, minimize the likelihood of puncturing a blood vessel wall, and increase the diameter of the reentry pathway distal to the occlusion.

In accordance with some examples, a catheter device can include a central catheter defining a central lumen and at least one reentry aperture. The central lumen can extend from a proximal end of the central catheter to a distal end of the central catheter, and can be configured to receive a primary guidewire for use as a guiding rail. The reentry aperture(s) can be oriented transverse to the extension of the central lumen. The catheter device can further include a first side tube and a second side tube, both coupled with the central catheter and extending along a longitudinal axis thereof. The first side tube can flank an opposite side of the central catheter relative to the second side tube. The catheter device can also include a subintimal guidewire extending in a curved configuration from the first side tube, distally beyond the distal end of the central catheter, to the second side tube. The subintimal guidewire can be made of, or coated with, a material viewable under fluoroscopy or other imaging means, and its shape can provide an indication to a user whether the reentry aperture(s) is properly oriented relative to a target blood vessel (i.e., toward the true lumen of the vessel). For example, if the shape of the subintimal guidewire forms a U-shape, indicating that the guidewire extends from the first side tube along a single curve or partial loop to the second side tube, proper catheter orientation may be present. If, on the other hand, the shape of the subintimal guidewire forms a complete loop (e.g., at least half of a FIG. 8 shape in which the guidewire crosses or encircles itself) as it extends from the first side tube to the second side tube, proper catheter orientation may not be present.

In some examples, the first side tube and the second side tube can comprise rods, and the subintimal guidewire can be attached to a distal face of the first side tube and a distal face of the second side tube. In some embodiments, two subintimal guidewires are included—a first guidewire extending through the first side tube and attached at its distal end to a first side of the central catheter, and a second guidewire extending through the second side tube and attached at its distal end to a second side of the central catheter. In some embodiments, the central catheter has a larger diameter than the first side tube and the second side tube. In some examples, a combined width of the central catheter, the first side tube and the second side tube is greater than a height of the central catheter. In some embodiments, the first side tube and the second side tube are equally sized. Some examples may further comprise a radiopaque marker. In some embodiments, a distal end of the central catheter is flush with a distal end of the first side tube and a distal end of the second side tube. In some examples, the distal end of the central catheter extends distally beyond a distal end of the first side tube and a distal end of the second side tube. In some embodiments, the distal end of the central catheter defines a tapered tip portion.

In accordance with some examples, a method for using the catheter device to bypass an occlusion in a blood vessel comprising a blood vessel wall defining a true lumen may involve first advancing a primary guidewire through the true lumen toward a proximal side of the occlusion. Methods may further involve loading the central catheter of the catheter device onto a proximal portion of the primary guidewire; advancing the catheter device over the primary guidewire toward the proximal side of the occlusion; upon reaching the proximal side of the occlusion, advancing the catheter device into a subintimal space within the blood vessel wall; urging the catheter device through the subintimal space until the distal end of the catheter device is positioned such that the first reentry aperture and the second reentry aperture are distal to the occlusion; advancing a reentry guidewire through the central lumen of the central catheter and out of a reentry aperture toward the true lumen distal to the occlusion; and removing the catheter device, optionally leaving the reentry guidewire in place.

In some embodiments, the reentry guidewire includes an integrated micro balloon, which may have a diameter of about 1 mm to about 5 mm, inclusive. Example methods may further involve removing the primary guidewire from the true lumen when the catheter device arrives at the proximal side of the occlusion, which may be a chronic total occlusion.

In accordance with some examples, a catheter assembly configured to form a subintimal track around an occlusion in a blood vessel may include: the catheter device described above, a primary guidewire configured to provide a rail to guide the catheter device to the proximal side of occlusion; and a reentry guidewire configured to exit the catheter device through an aperture and reenter the true lumen distal to the occlusion.

BRIEF DESCRIPTION OF THE DRAWINGS

In the drawings, like numerals can be used to describe similar features and components throughout the several views. The drawings illustrate generally, by way of example but not by way of limitation, various embodiments discussed in this patent document:

FIG. 5 illustrates a schematic view, in longitudinal cross-section, of a subintimal track around an occlusion, with reentry into the natural blood vessel lumen at a location distal of the occlusion.

FIG. 6 illustrates a transverse cross-section of a coronary artery containing an occlusion and a subintimal track around the occlusion, such as a cross-section taken along line 6-6 of FIG. 5.

Figure 1:
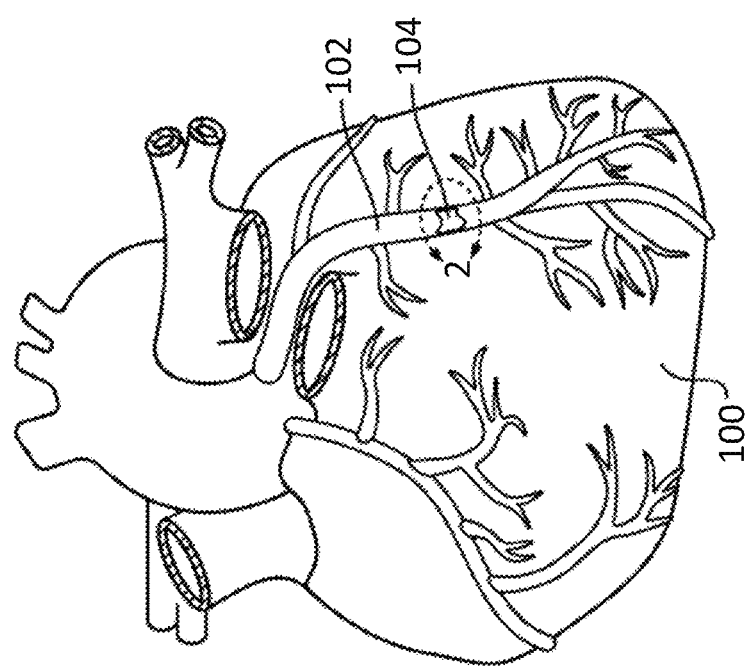
FIG. 1 illustrates a schematic view of a heart, including a coronary artery containing an occlusion.

The drawing figures are not necessarily to scale. Certain features and components may be shown exaggerated in scale or in schematic form, and some details may not be shown in the interest of clarity and conciseness.

DETAILED DESCRIPTION

Definitions

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "distal" and "proximal" refer to a position or direction relative to a user, e.g., a treating clinician. "Distal" and "distally" refer to a position that is distant, or in a direction away, from the clinician. "Proximal" and "proximally" refer to a position that is closer to, or in a direction toward, the clinician.

The term "patient" refers to a mammal and includes both humans and animals.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.), and all numbers included within ranges are modified by the term "about," even if not expressly stated, unless otherwise indicated.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The present disclosure provides catheter devices, assemblies and associated methods for crossing or bypassing total or near occlusions formed in a natural vessel lumen with diminished risk of vessel wall perforation and with a minimum number of separate medical devices. The catheter device can include a central catheter flanked by two side tubes and a subintimal guidewire that forms a curved structure projecting from a distal end of the device. The subintimal guidewire can facilitate entry into a subintimal space adjacent an occlusion, help orient the device within the subintimal space, and guide the device through the subintimal space, thereby forming a generally planar subintimal track. The central catheter can define two reentry apertures configured as outlet passages for a reentry guidewire to exit the device, cross the intimal layer, and reenter the true lumen of the blood vessel distal to the occlusion. The reentry guidewire can include an integrated micro balloon in at least some examples to increase the diameter of the reentry lumen formed through the intimal layer.

The present devices and assemblies may be used in various blood vessel types, e.g., coronary arteries, peripheral arteries and veins, for the treatment of coronary and peripheral vascular diseases and arterio-venous grafts, for example.

FIG. 1 illustrates a schematic view of a heart 100, including a coronary artery 102 containing an occlusion 104. As used herein, an "occlusion" may be a total occlusion (e.g., a CTO), near total occlusion, or partial blockage of a blood vessel.

Figure 2:
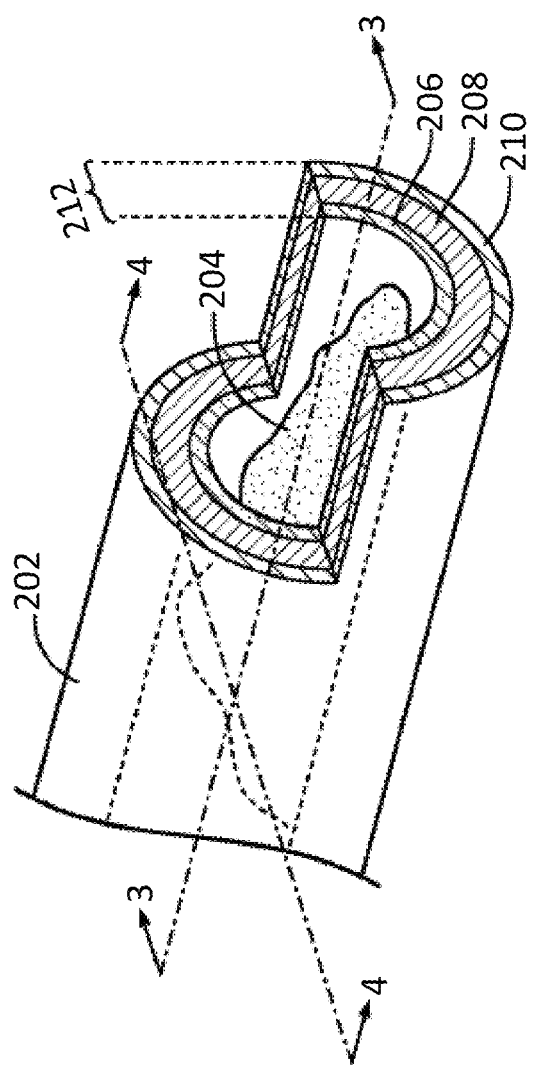
FIG. 2 illustrates a schematic view of a coronary artery containing an occlusion and the artery's intimal, medial and adventitial wall layers.

FIG. 2 illustrates a schematic view of a coronary artery 202 containing an occlusion 204. The coronary artery's wall 212 includes intimal 206, medial 208 and adventitial 210 layers. Concentrically outward of the intima 206 is the medial layer 208. The transition between the external most portions of the intima 206 and the internal most portions of the medial 208 can be referred to as the subintimal region. The outermost layer of the artery is the adventitia 210.

The anatomy of a venous wall is similar to the anatomy of an arterial wall with two primary exceptions. First, arterial walls are thicker than venous walls to withstand higher pressures produced from heartbeats. Second, an endothelium layer on an inner surface of the intima of a vein includes one or more valves. Since blood in veins flows against gravity, the valves prevent backflow and keep blood moving toward the heart. The similarities between venous and arterial wall anatomies allow the present devices, assemblies and methods to be used in a similar manner in both vessel types.

Figure 3:
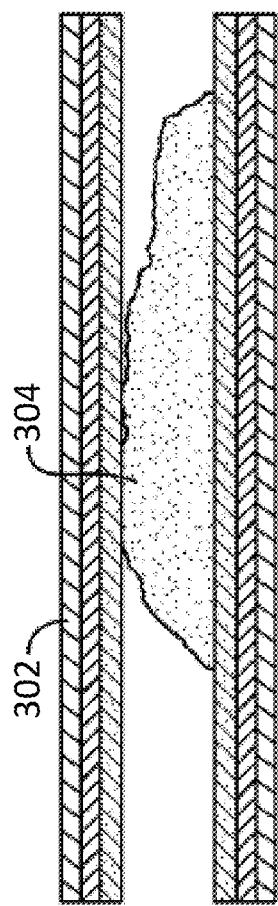
FIG. 3 illustrates a longitudinal cross-section of a coronary artery containing an occlusion, such as a cross-section taken along line 3-3 of FIG. 2.
Figure 4:
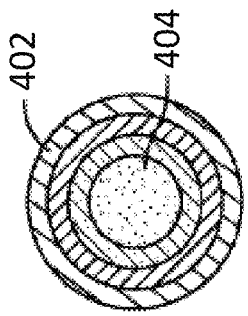
FIG. 4 illustrates a transverse cross-section of a coronary artery containing an occlusion, such as a cross-section taken along line 4-4 of FIG. 2.

FIGS. 3 and 4 illustrate cross-sections of a coronary artery 302, 402 containing an occlusion 304, 404 in the form of a CTO. FIG. 3 is a longitudinal cross-section taken along line 3-3 of FIG. 2. FIG. 4 is a transverse cross-section taken along line 4-4 of FIG. 2. It is believed that the present devices and related methods can provide utility in the successful treatment of CTOs or near total blockages of blood vessels.

FIG. 5 illustrates a schematic view, in longitudinal cross-section, of a subintimal track 514 established around an occlusion 504 within a coronary artery 502. Using a minimally invasive technique made possible by the present devices, assemblies and methods, the subintimal track 514 can be created between the external most portions of the intimal layer 506 and the internal most portions of the medial wall 508 of the arterial wall 512. The track 514 can reenter the true lumen of the artery 502 at a location distal of the occlusion 504. Eventually, the subintimal track 514 formed using the devices, assemblies and methods described herein can become the permanent vascular pathway around the CTO 504, thus allowing blood to flow through the vessel despite the continued presence of the CTO.

FIG. 6 is a transverse cross-section taken along line 6-6 of FIG. 5 and illustrates a subintimal track 614 created around a CTO 604 within a coronary artery 602. The subintimal track 614 is shown between the external most portions of the intimal layer 606 and the internal most portions of the medial layer 608.

The term "guidewire" as used herein is to be broadly construed to include wire-like structures of dimension and length that are intended to safely navigate through or around an occlusion in a blood vessel. The wire-like structures can include, but are not limited to, diagnostic, therapeutic or interventional guidewires, wire guides, spring wires, exchange guidewires and extension wires. Transverse dimensions of the guidewires can primarily fall in the range of about 0.025 cm (0.010 in) to about 0.089 cm (0.035 in) in diameter and about 30 cm to about 300 cm (or more) in length. The guidewires can be coated or treated with various compositions (e.g., polymers or other compounds) to change their handling or performance characteristics, such as to increase lubricity, to increase or decrease hydrophobicity, or to reduce thrombogenicity of portions of their external surface. A hydrophilic polymer in the form of polyvinylpyrrolidone, for example, can exhibit lubricity when moistened. A polymer in the form of polytetrafluoroethylene (PTFE) can reduce the coefficient of friction. The guidewires can also remain uncoated and untreated.

Figure 7:
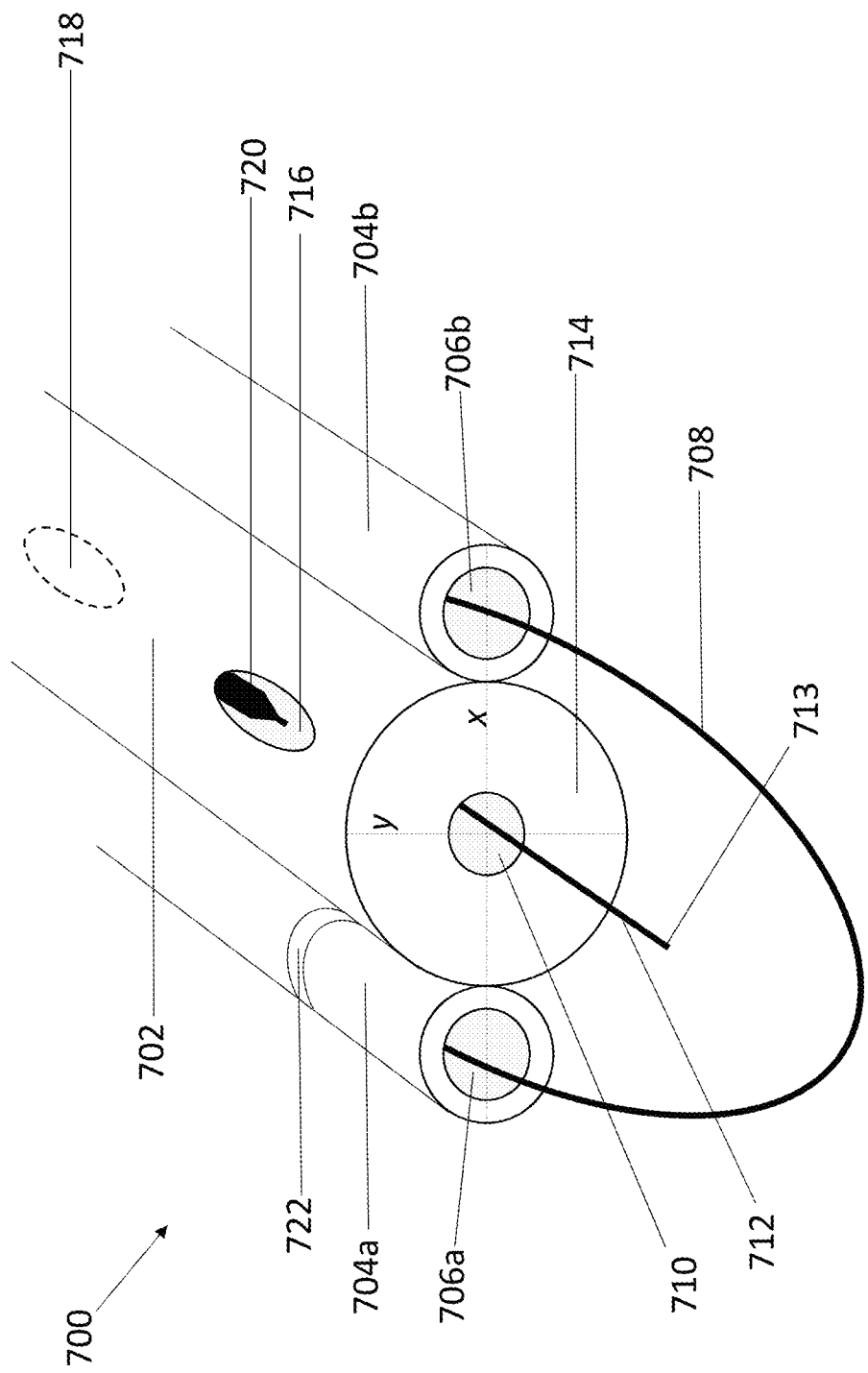
FIG. 7 illustrates an isometric view of a portion of the distal end of a catheter device, a primary guidewire and a reentry guidewire, as constructed in accordance with at least one embodiment.

FIG. 7 illustrates the distal end of a catheter device 700, which is configured to create a subintimal track around a blood vessel occlusion and facilitate reentry into the true lumen of the vessel distal to the occlusion. The device 700 includes a central catheter 702, which can comprise an elongate, flexible material, flanked by a pair of side tubes 704a, 704b, each side tube defining a central lumen 706a, 706b. The device 700 further includes a subintimal guidewire 708 that can extend through the side tubes 704a, 704b and assume a curved shape in front of the central catheter 702, which also defines a central lumen 710 through which a primary guidewire 712 can extend. Ends of the subintimal guidewire 708 can be positioned near a proximal end of the central catheter 702 for manipulation by a user. In some uses, the ends of the subintimal guidewire 708 can be urged distally so that a size of the curved shape is wider than a collective width of the central catheter 702 and the pair of side tubes 704a, 704b. The curvature and the ability to control the size of the curvature of the subintimal guidewire 708 allows the user to control the size of the subintimal delamination track—too large of a subintimal track may not allow the catheter device to be oriented properly to gain reentry to the true lumen of a vessel, and too small of a subintimal track may not allow the catheter device to be distally advanced. The primary guidewire 712 passes through the vasculature, providing a rail that guides the device 700 to the occlusion site. At its most distal end, the central catheter 702 can further define a leading face 714, which may be flat or tapered and optionally metallic. The body of the central catheter 702 can also define a first reentry aperture 716 and a second reentry aperture 718. As shown, the first reentry aperture 716 may be positioned on an opposite side of the central catheter 702 relative to the second reentry aperture 718, such that depending on the orientation of the device 700 relative to the vessel, one aperture can be positioned on the top side of the device, away from the true lumen, and the other aperture can be positioned on the bottom side of the device, toward the true lumen. The distal end of a reentry guidewire 720 is shown visible through the first reentry aperture 716.

The central catheter 702, side tubes 704a, 704b, and subintimal guidewire 708, in combination, define an oblong, generally planar shape of the device 700. This shape is configured to cross the intimal layer of an occluded blood vessel without overextending across the medial layer. By advancing it through the subintimal space, the device 700 creates the subintimal track and can orient one of the two reentry apertures 716 or 718 to face the true lumen. A shape of the subintimal guidewire 708, viewable under fluoroscopy or other imaging means, can indicate to the user whether a reentry aperture is properly oriented relative to the vessel's true lumen. For example, if the shape of the subintimal guidewire forms a U-shape, indicating that the guidewire extends from the first side tube along a single curve to the second side tube, proper catheter orientation may be present. If, on the other hand, the shape of the subintimal guidewire forms a complete loop (e.g., at least half of a FIG. 8 shape in which the guidewire crosses or encircles itself) as it extends from the first side tube to the second side tube, proper catheter orientation may not be present. The cross-sectional diameter x of the device 700, defined by the total diameter of the central catheter 702 and both side tubes 704a, 704b, can be greater than the height y of the central catheter 702. The central catheter 702 may have a greater diameter than each of the side tubes 704a, 704b, which may be identical or similar in size.

Figure 8:
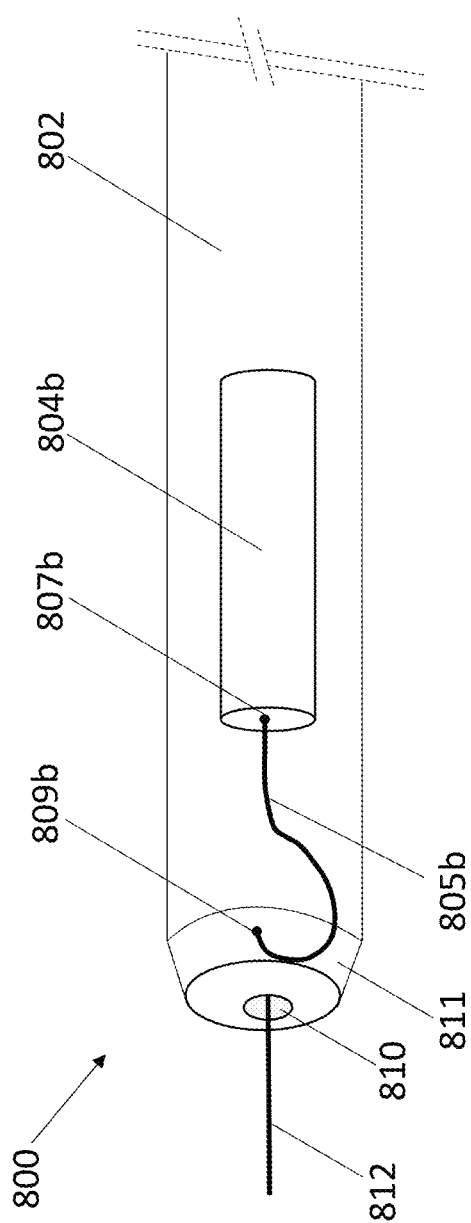
FIG. 8 illustrates an isometric side view of a portion of the distal end of a catheter device and a primary guidewire, as constructed in accordance with at least one embodiment.

The length and/or position of the side tubes 704a, 704b can vary. For example, the arrangement of the side tubes 704a, 704b relative to the central catheter 702 may be different than the arrangement shown in FIG. 7, which depicts the side tubes 704a, 704b arranged symmetrically on opposite sides of the central catheter 702. For example, as shown in FIG. 8, the side tubes can be offset from the distal end of the central catheter 702 such that the distal ends of the side tubes are not flush with the distal face 714 of the central catheter. In some embodiments, the side tubes may extend the entire length of the central catheter 702, while in other embodiments, the side tubes may only extend for a defined length near the distal end of the device 700. The length of the side tubes may also vary depending on the length of the targeted occlusion. Longer occlusions, for example, may be treated with devices having longer side tubes. In various embodiments, the central catheter and/or the side tubes may have a length ranging from about 30 cm to about 300 cm. In some examples, the side tubes may have a length ranging from about 0.5 to about 1, about 2, about 5, about 10, about 15, about 20, about 25, or about 30 cm. In addition, or alternatively, the side tubes may define metallic tip portions, which may be flat or tapered.

In at least some examples, portions or all of the central catheter 702 and/or side tubes 704a, 704b can be doped with, made of, or otherwise include a radiopaque material. Radiopaque materials are capable of producing a relatively bright image on a fluoroscopy screen or other imaging display during a medical procedure. This relatively bright image aids the user in determining its location and in some embodiments, orientation. Some examples of radiopaque materials can include, but are not limited to, gold, platinum, palladium, tantalum, tungsten alloy, polymer material loaded with radiopaque filler, and the like. Additionally, other radiopaque marker bands or coils can also be incorporated into the design of the device to achieve the same or similar result. In some examples, one or more marker bands, such as marker band 722, can be included on the device 700 to aid a user in determining the orientation of the device. As shown, one or more marker bands may be positioned on side tube 704a or 704b. Alternatively, marker bands may be included at different positions on both side tubes or the central catheter 702.

In some embodiments, a degree of Magnetic Resonance Imaging (MRI) compatibility is imparted into the device 700 to enhance compatibility with MRI machines. For example, the central catheter 702, the side tubes 704a, 704b, and/or portions thereof can be made of a material that does not substantially distort the guidewire image or create substantial artefacts (or gaps) in the device image. Suitable materials can include tungsten, cobalt-chromium-molybdenum alloys, nickel-cobalt-chromium-molybdenum allows, nitinol, and the like.

The device 700 should allow a user to steer the structure through the branches of a subject's blood vessels and manipulate it to a diseased site in an intended vessel. Additionally, the device should be sufficiently flexible to pass through sharply curved tortuous coronary anatomy, as well as to provide a sufficiently soft leading tip that will not injure vessel wall tissue during use. Further, the subintimal guidewire 712 should have sufficient column strength so that it can be pushed or otherwise urged without kinking. In some examples, the subintimal guidewire 712 may comprise nitinol. Nitinol may not kink during operation, and has a stiffness that maintains the curved or partially looped shape of the subintimal guidewire when navigating through the vasculature and pushing through the subintimal space.

In operation, the primary guidewire 712 can be advanced through a patient's vasculature toward a proximal side of an occlusion until the distal end 713 of the guidewire reaches the occlusion. A user manipulating the primary guidewire can determine that it has arrived at the occlusion by feel and/or through the use of various imaging techniques, which may involve detection of the distal end of the primary guidewire. Once the distal end 713 of the primary guidewire 712 reaches the proximal side of the occlusion, the device 700 can be fed over the primary guidewire 712 by first inserting a proximal end of the primary guidewire into the central lumen 710 of the central catheter 702, and then sliding the central catheter over the primary guidewire in rail-like fashion toward the occlusion. Upon arriving at the occlusion, the primary guidewire 712 can be removed from the blood vessel, leaving the distal end of the device 700 at the occlusion site.

Led by the subintimal guidewire 708, the distal end of the device 700 can then be urged into the subintimal space adjacent to the occlusion, creating a space or track for the remainder of the device to follow. The curved shape and large leading radius of the guidewire 708 reduces the risk of perforating the vessel wall, and upon entering the subintimal space, creates a subintimal plane through which the user can continue to advance the device 700 distally around the occlusion. As the subintimal guidewire 708 is further advanced by a proximally-applied force, a delamination plane between the intimal and medial layers is created around the occlusion. The curvature of the subintimal guidewire 708 helps to minimize the possibility of penetrating the medial layer as the device is advanced distally.

Collectively, the side tubes 704a, 704b, the curved configuration of the subintimal guidewire 708 and the user's ability to control the length or amount of curvature of the guidewire 708 help orient the device within the subintimal plane, such that the first reentry aperture 716 faces away from the true lumen of the blood vessel, and the second reentry aperture 718 faces toward the true lumen, or vice versa. In this manner, the horizontal axis x of the device 700 defines the width of the subintimal track and the vertical axis y defines the height of the subintimal track.

Once the reentry apertures 716, 718 are both advanced distally passed the occlusion, the reentry guidewire 720 can be advanced through the central lumen 710. The reentry guidewire 720 is configured to exit the central lumen 710 through the first reentry aperture 716 or the second reentry aperture 718, but the user only extends the reentry guidewire through the reentry aperture that faces the true lumen of the vessel. In some examples, the user can make this determination based on feel. In particular, the tissue of the medial layer is noticeably tougher and firmer than the tissue comprising the intimal layer. As such, the user may feel more resistance when attempting to push the reentry guidewire 720 toward the medial layer compared to the intimal layer. Any noticeable resistance thus serves as an indication to the user that the reentry guidewire 720 should be passed through the other reentry aperture, toward the intimal layer and into the true lumen. After exiting the central lumen 710 through the correct aperture, the reentry guidewire 720 passes through the intimal wall and back into the true lumen, thus creating a reentry lumen through the intimal wall and completing the subintimal track pathway from a proximal side to a distal side of the occlusion. The diameter of the reentry guidewire 720 can determine the diameter of the reentry lumen. To eliminate the need for the user to move the reentry guidewire in a circular, back-and-forth, or whiplash like motion in an attempt to increase the diameter of the reentry lumen, the reentry guidewire can have a larger diameter than other guidewires or catheters used for luminal reentry in existing devices. In some examples, the reentry guidewire can include an integrated micro balloon. The diameter of the micro balloon may vary depending on the intended diameter of the reentry lumen formed in the vessel wall. In some examples, the diameter of the micro balloon may range from about 1 to about 15 mm, about 1 to about 10 mm, or about 1 to about 5 mm.

After bypassing the occlusion, treatment methods may further involve removing the catheter device 700 from the blood vessel, optionally swapping the reentry guidewire 720 for a primary guidewire, and advancing the distal end of a catheter or other treatment device over the reentry guidewire 720 or the primary guidewire to a location near the distal side of the occlusion. The catheter or other treatment device can be guided around the occlusion using the reentry guidewire 720 or the primary guidewire as a rail and subsequently used to perform balloon angioplasty, stenting, atherectomy, or another endovascular treatment method for compressing and opening the occlusion region via the subintimal track.

FIG. 8 illustrates an isometric side view of a portion of the distal end of another catheter device 800 configured to form a subintimal track around an occlusion. The device 800 includes a central catheter 802 defining a central lumen 810 flanked by a pair of side tubes (only side tube 804b is visible from this viewing angle). A primary guidewire 812 extends through the central lumen 810. The side tubes can be offset relative to the distal end of the central catheter 802 and, as further shown, can have a length that spans only portion of the length of the central catheter. The side tubes, e.g., side tube 804b, comprise a solid rod in this embodiment, to which a lateral subintimal guidewire 805b can be attached (another lateral subintimal guidewire 805a is included on the opposite side of the device). Specifically, one end of the lateral subintimal guidewire 805b can be attached to the side tube 804b at a proximal attachment point 807b, and a second end of the lateral subintimal guidewire 805b can be attached to a tapered surface 811, which may be metallic, of the central catheter 802 at a distal attachment point 809b. The lateral subintimal guidewire 805b can be configured to have a curved, partially looped shape. The configuration of the device 800 is identical on both sides, such that first and second lateral subintimal guidewires 805a, 805b are included. The distal end of the central catheter, along with the pair of lateral subintimal guidewires, form a curved shape and relatively large leading radius, similar to that provided by the subintimal guidewire 708 shown in FIG. 7. Together, the lateral subintimal guidewires and/or central catheter can function similarly to the subintimal guidewire 708 of FIG. 7 in response to distal advancement of the device 800 by a user, i.e., by entering the subintimal space, creating the subintimal track, and facilitating reentry into the true lumen via advancement of a reentry guidewire through one of two reentry apertures defined by the device. The distance that the lateral subintimal guidewires extend distally can vary. For example, the most distal point of the guidewires may be flush with the most distal point of the central catheter. Alternatively, the guidewires may extend distally beyond the most distal point of the central catheter.

In some embodiments, the lateral subintimal guidewires may protrude laterally away from the external wall of the central catheter.

Figure 9:
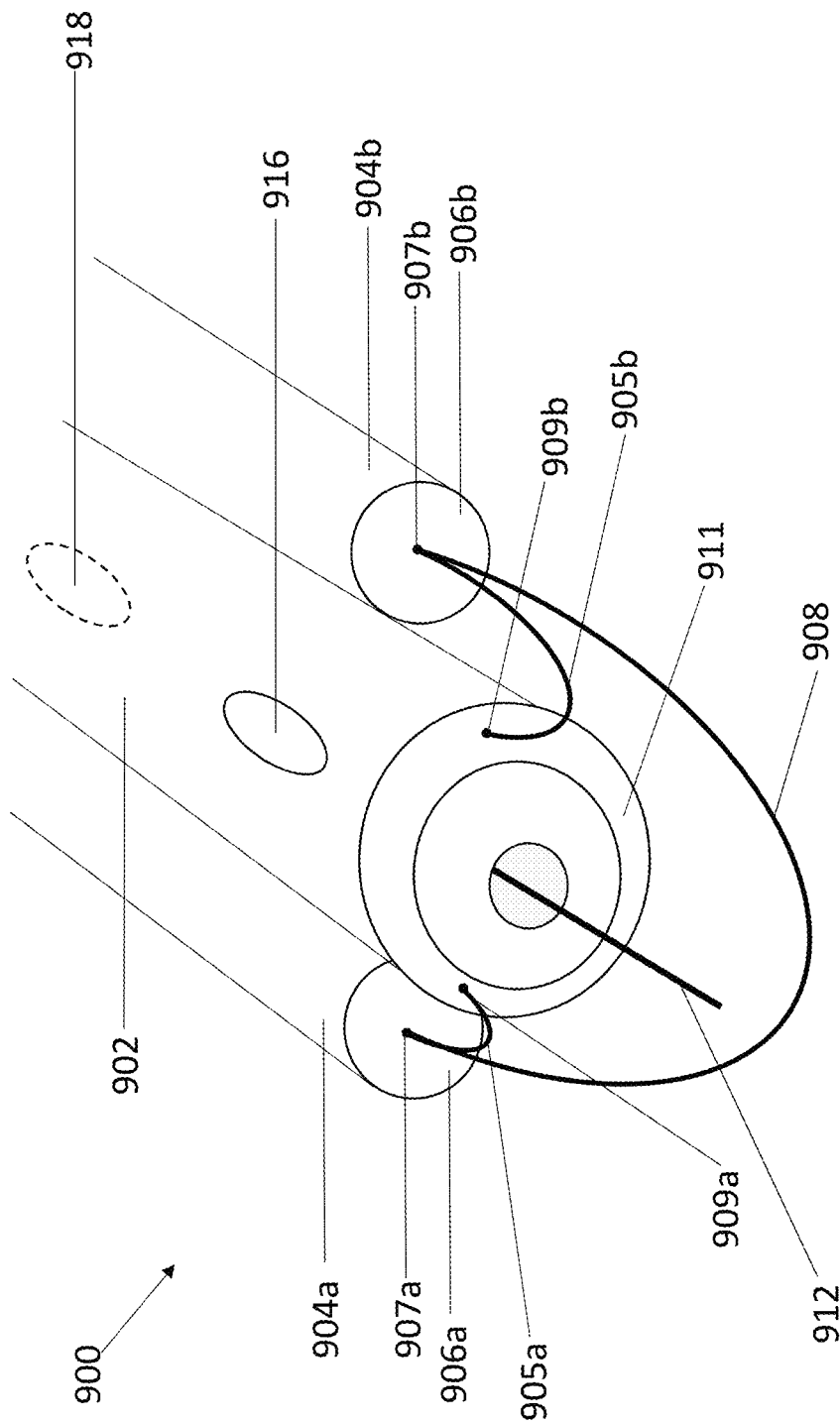
FIG. 9 illustrates an isometric view of a portion of the distal end of a catheter device and a primary guidewire, as constructed in accordance with at least one embodiment.

FIG. 9 illustrates an isometric view of a portion of the distal end of another catheter device 900 configured to form a subintimal track around an occlusion. Like the device 800 shown in FIG. 8, the device 900 includes a central catheter 902 flanked by a pair of rod-like side tubes 904a, 904b, each defining a distal face 906a, 906b instead of a central lumen. A primary guidewire 912 can extend through a central lumen of the central catheter 902. The body of the central catheter 902 can also define a first reentry aperture 916 and a second reentry aperture 918. The device 900 also includes a pair of lateral subintimal guidewires 905a, 905b extending respectively from proximal attachment points 907a, 907b on the distal faces 906a, 906b of the side tubes 904a, 904b to distal attachment points 909a, 909b on a tapered surface 911 of the central catheter. Like the device 700 shown in FIG. 7, a longer subintimal guidewire 908 may also be included, forming a curved structure around the distal end of the central catheter. In operation, the device 900 can function similar to the devices 700, 800, described above.

Figure 10:
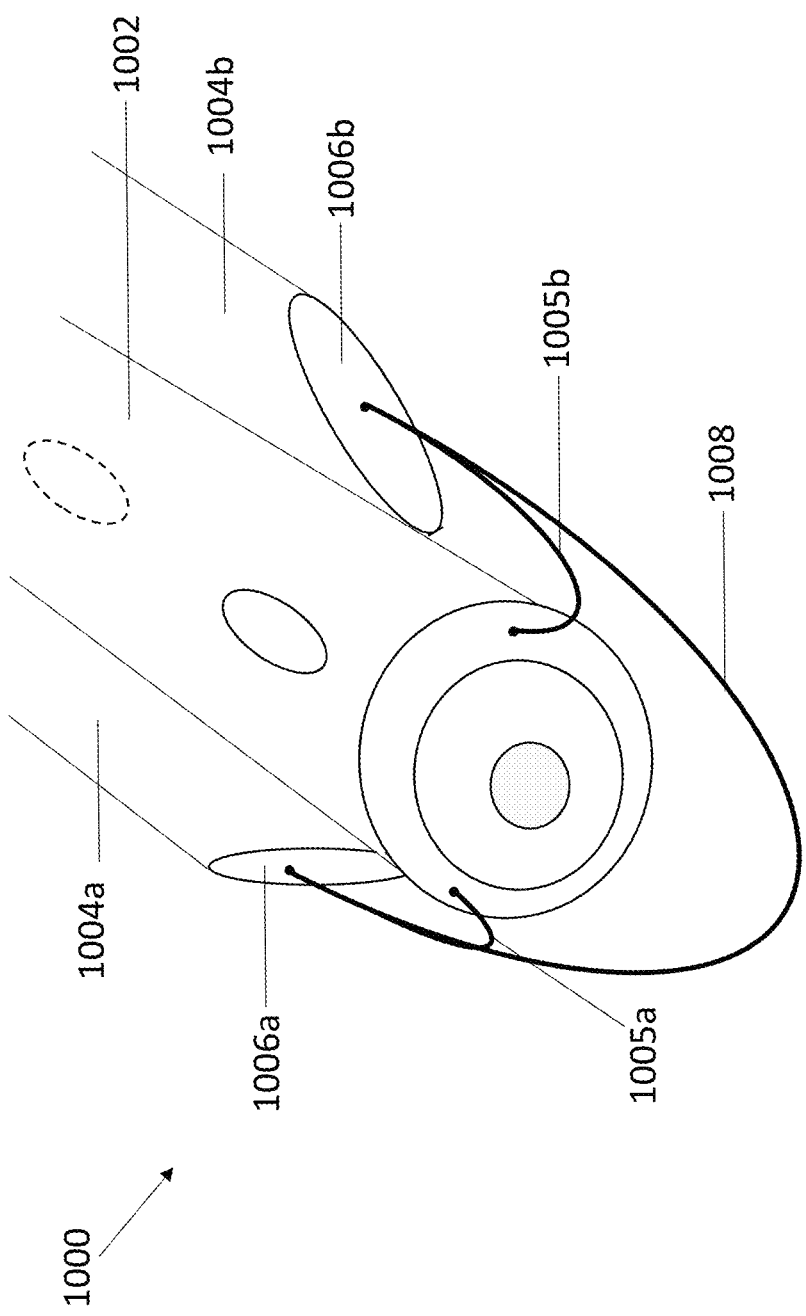
FIG. 10 illustrates an isometric view of a portion of the distal end of a catheter device, as constructed in accordance with at least one embodiment.

FIG. 10 illustrates an isometric view of a portion of the distal end of another catheter device 1000 configured to form a subintimal track around an occlusion. As shown, the device 1000 includes a central catheter 1002 and a pair of side tubes 1004a, 1004b. The device 1000 can further include lateral subintimal guidewires 1005a, 1005b and a longer subintimal guidewire 1008. The side tubes 1004a, 1004b can define various shapes. In this particular example, the side tubes 1004a, 1004b define slanted distal surfaces 1006a, 1006b to facilitate smooth passage through the intimal layer and subintimal space. While the side tubes are portrayed herein as being generally cylindrical, the side tubes can also or instead by any suitable or desired shape, including fin-shaped, triangular, wedge, rectangular, etc. In operation, the device 1000 can function similar to the devices 700, 800, 900, described above.

Closing Notes and Examples

Cardiovascular disease, including atherosclerosis, is a leading cause of death in the United States and elsewhere. A method for treating atherosclerosis and other forms of vessel lumen narrowing is angioplasty. The objective of angioplasty is to restore adequate blood flow through the affected vessel. The present devices, assemblies and related methods allow for treating an occlusion, particularly a CTO, using a reduced number of separate medical devices, while minimizing the likelihood of vessel wall dissection and increasing the diameter of a reentry pathway distal to the occlusion.

The above Detailed Description includes references to the accompanying drawings, which form a part of the Detailed Description. The Detailed Description should be read with reference to the drawings. The drawings show, by way of illustration, specific embodiments in which the present devices, assemblies and methods can be practiced. These embodiments are also referred to herein as "examples."

Although the present invention has been described with reference to certain embodiments, persons skilled in the art will recognize that changes may be made in form and detail without departing from the spirit and scope of the invention. For example, a wide variety of modifications to the embodiments of the present disclosure may be made with respect to, for example, the sequence of method steps and configuration of the percutaneous instruments employed during one or more of these steps.

The Detailed Description is intended to be illustrative and not restrictive. For example, the above-described examples (or one or more features or components thereof), can be used in combination with each other. Other embodiments can be used, such as by one of ordinary skill in the art upon reviewing the above Detailed Description. Also, various features or components have been or can be grouped together to streamline this disclosure. This should not be interpreted as intending that the unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a catheter device can include a central catheter defining: a central lumen extending from a proximal end of the central catheter to a distal end of the central catheter, the central lumen configured to receive a primary guidewire; and at least one reentry aperture oriented transverse to the extension of the central lumen. The catheter device can further include a first side tube and a second side tube both coupled with the central catheter and extending along a longitudinal axis thereof. The first side tube can flank an opposite side of the central catheter relative to the second side tube. A subintimal guidewire can extend from the first side tube, distally beyond the distal end of the central catheter, to the second side tube.

In Example 2, the catheter device of Example 1 can optionally be configured such that ends of the subintimal guidewire extend to a position near the proximal end of the central catheter and are configured to receive and translate an externally-applied pushing or pulling force.

In Example 3, the catheter device of any one of Examples 1 or 2 can optionally be configured such that the first side tube and the second side tube comprise rods, and ends of the subintimal guidewire can be attached to a distal face of the first side tube and a distal face of the second side tube.

In Example 4, the catheter device of any one of Examples 1-3 can optionally be configured such that the central catheter has a larger diameter than a diameter of the first side tube and a diameter of the second side tube.

In Example 5, the catheter device of Example 4 can optionally be configured such that a combined width of the central catheter, the first side tube and the second side tube is greater than a height of the central catheter.

In Example 6, the catheter device of Example 4 can optionally be configured such that the first side tube and the second side tube are equally sized.

In Example 7, the catheter device of any one or any combination of Examples 1-6 can optionally further comprise a radiopaque marker.

In Example 8, the catheter device of any one or any combination of Examples 1-7 can optionally be configured such that a distal end of the central catheter is flush with a distal end of the first side tube and a distal end of the second side tube.

In Example 9, the catheter device of any one or any combination of Examples 1-7 can optionally be configured such that the distal end of the central catheter extends distally beyond a distal end of the first side tube and a distal end of the second side tube.

In Example 10, the catheter device of any one or any combination of Examples 1-9 can optionally be configured such that the distal end of the central catheter defines a tapered tip portion.

In Example 11, the catheter device of any one or any combination of Examples 1-10 can optionally be configured such that the subintimal guidewire defines a partial loop that extends distally beyond the distal end of the central catheter.

In Example 12, a method for using a catheter device according to any one or any combination of Examples 1-11 to bypass an occlusion in a blood vessel comprising a blood vessel wall defining a true lumen can involve advancing a primary guidewire through the true lumen toward a proximal side of the occlusion; loading the central catheter of the catheter device onto a proximal portion of the primary guidewire; advancing the catheter device over the primary guidewire toward the proximal side of the occlusion; upon reaching the proximal side of the occlusion, advancing the catheter device into a subintimal space within the blood vessel wall; urging the catheter device through the subintimal space until a distal end of the catheter device is positioned such that the first reentry aperture and the second reentry aperture are distal to the occlusion; advancing a reentry guidewire through the central lumen of the central catheter and out of a reentry aperture toward the true lumen distal to the occlusion; and removing the catheter device.

In Example 13, the method of Example 12 can optionally be configured such that the reentry guidewire includes an integrated micro balloon.

In Example 14, the method of Example 13 can optionally be configured such that the micro balloon has a diameter of about 1 mm to about 5 mm.

In Example 15, the method of any one or any combination of Examples 12-14 can optionally further involve removing the primary guidewire from the true lumen when the catheter device arrives at the proximal side of the occlusion.

In Example 16, the method of any one or any combination of Examples 12-15 can optionally be configured to be employed where the occlusion is a chronic total occlusion.

In Example 17, a catheter assembly configured to form a subintimal track around an occlusion in a blood vessel can include the catheter device of any one or any combination of Examples 1-11; a primary guidewire configured to provide a rail for the catheter device; and a reentry guidewire configured to exit the catheter device and reenter the true lumen distal to the occlusion.

The scope of the present devices, assemblies and methods should be determined with reference to the appended claims, along with the full scope of equivalents to which such claims are entitled. In the appended claims, the terms "including" and "in which" are used as the plain-English equivalents of the respective terms "comprising" and "wherein." Also in the following claims, the terms "including" and "comprising" are open-ended; that is, a device, assembly or method that includes features or components in addition to those listed after such a term in a claim are still deemed to fall within the scope of that claim. Moreover, the terms "first," "second" and "third," etc. in the following claims are used merely as labels, and such terms are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A catheter device comprising:
    a central catheter defining:
        a central lumen extending from a proximal end of the central catheter to a distal end of the central catheter, the central lumen configured to receive a primary guidewire, and
        at least one reentry aperture oriented transverse to the extension of the central lumen;

a first side tube and a second side tube, each coupled with and extending alongside the central catheter and extending along a longitudinal axis thereof, the first side tube flanking an opposite side of the central catheter relative to the second side tube; and a subintimal guidewire extending from the first side tube, distally beyond the distal end of the central catheter, to the second side tube.

2. The catheter device of claim 1, wherein ends of the subintimal guidewire extend to a position near the proximal end of the central catheter and are configured to receive and translate an externally-applied pushing or pulling force.

3. The catheter device of claim 1, wherein the first side tube and the second side tube comprise rods, and wherein ends of the subintimal guidewire are attached to a distal end of the first side tube and a distal end of the second side tube.

4. The catheter device of claim 1, wherein the central catheter has a larger diameter than a diameter of the first side tube and a diameter of the second side tube.

5. The catheter device of claim 4, wherein a combined width of the central catheter, the first side tube and the second side tube is greater than a height of the central catheter.

6. The catheter device of claim 1, further comprising a radiopaque marker.

7. The catheter device of claim 6, wherein a portion of at least one of the central catheter, the first side tube, or the second side tube is doped with or made of the radiopaque marker.

8. The catheter device of claim 6, wherein the radiopaque marker includes a marker band positioned on at least one of the central catheter, the first side tube, or the second side tube.

9. The catheter device of claim 1, wherein the distal end of the central catheter is flush with a distal end of the first side tube and a distal end of the second side tube.

10. The catheter device of claim 1, wherein the distal end of the central catheter extends distally beyond a distal end of the first side tube and a distal end of the second side tube.

11. The catheter device of claim 1, wherein the distal end of the central catheter defines a tapered tip portion.

12. The catheter device of claim 1, wherein a distal end of the first side tube and a distal end of the second side tube each define a slanted distal surface.

13. The catheter device of claim 1, wherein at least one of the distal end of the central catheter, a distal end of the first side tube, or a distal end of the second side tube define a metallic tip.

14. The catheter device of claim 1, wherein the subintimal guidewire defines a partial loop that extends distally beyond the distal end of the central catheter.

15. The catheter device of claim 1, further comprising a pair of lateral subintimal guidewires, each extending from a proximal attachment point on a distal end of the first or second side tube to a distal attachment point on a surface of the central catheter.

16. The catheter device of claim 15, wherein the subintimal guidewire extends further distally than the pair of lateral subintimal guidewires.

17. The catheter device of claim 15, wherein the most distal point of the lateral subintimal guidewires is flush with the distal end of the central catheter.

18. The catheter device of claim 15, wherein the most distal point of the lateral subintimal guidewires extends distally beyond the distal end of the central catheter.

19. A method for using a catheter device according to claim 1 to bypass an occlusion in a blood vessel comprising a blood vessel wall defining a true lumen, the method comprising:

advancing a primary guidewire through the true lumen toward a proximal side of the occlusion;

loading the central catheter of the catheter device onto a proximal portion of the primary guidewire;

advancing the catheter device over the primary guidewire toward the proximal side of the occlusion;

upon reaching the proximal side of the occlusion, advancing the catheter device into a subintimal space within the blood vessel wall;

urging the catheter device through the subintimal space until a distal end of the catheter device is positioned such that the first reentry aperture and the second reentry aperture are distal to the occlusion;

advancing a reentry guidewire through the central lumen of the central catheter and out of a reentry aperture toward the true lumen distal to the occlusion; and removing the catheter device.

20. The method of claim 19, wherein urging the catheter device through the subintimal space includes manipulating ends of the subintimal guidewire to control a size of a curved shape of the subintimal guidewire extending distal to the central catheter.

21. A catheter assembly configured to form a subintimal track around an occlusion in a blood vessel, the catheter assembly comprising:

the catheter device according to claim 1;

a primary guidewire configured to provide a rail for the catheter device; and a reentry guidewire configured to exit the catheter device and reenter the true lumen distal to the occlusion.

22. The catheter assembly of claim 21, wherein the reentry guidewire includes an integrated micro balloon.

* * * * *